US00PP10601P

United States Patent [19]

Tucker

[11] Patent Number: Plant 10,601

[45] Date of Patent: Sep. 15, 1998

[54] MINIATURE ROSE PLANT NAMED 'TUCKFLIP'

[76] Inventor: Robert T. Tucker, 9404 Hunting Hills Dr., Franklin, Tenn. 37607

[21] Appl. No.: 863,591

[22] Filed: May 27, 1997

[51] Int. Cl.[6] ..... A01H 5/00

[52] U.S. Cl. ..... Plt./10

[58] Field of Search ..... Plt./10, 10.1, 7.1

*Primary Examiner*—Howard J. Locker

[57] ABSTRACT

This invention relates to a new and distinct variety of miniature rose plant primarily identified by its medium red buds and flowers, Hybrid Tea form and glossy green foliage.

1 Drawing Sheet

The present invention relates to a new and distinct variety of hardy, dwarf, bush type rose plant of the miniature class; the variety being primarily characterized—as to novelty—by buds and flowers of a uniform medium red color which generally are of exhibition (Hybrid Tea) form.

The variety is further characterized by:

An abudundance of bloom, with flowers often borne singly and also several to the stem in loose clusters.

No fragrance.

A plant which is vigorous, of rounded, upright shape with medium growth habit and glossy foliage.

The plant, which has a normal height of 18–24 inches can easily be maintained at lesser height by occasional trimming.

A plant which grows and blooms satisfactorily both in the greenhouse and outdoors; is good for growing in pots; and provides excellent garden decoration as well as cut flowers.

The present variety of miniature rose was originated by me in my hybridizing garden located at Franklin, Tenn. under conditions of careful control and observation, as a cross between Elizabeth Taylor Hybrid Tea— U.S. Plant Pat. No. 6,492) as the seed parent and BENMagic (a.k.a. Kristin™)(Miniature—U.S. Plant Pat. No. 8,603) as the pollen parent. Subsequent to origination of the variety, I successfully asexually reproduced it at my hybridizing garden, located as aforesaid, by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plant identifications being by reference to The Royal Horticultrual Society Colour Chart, except where common terms of color definition are employed.

Class: Miniature.

*Variety identification.*—TUCkflip.

(*Commercial synonym.*—Miss Flippins).

FLOWER

Observations made from specimens grown in a garden environment at Franklin, Tenn. in May 1995 through October 1996.

Blooming habit: Continuous.

Bud:

*Size.*—¾ to 1 inch long when the petals start to unfurl.

*Form.*—The bud form is long and tapered.

*Color.*—When sepals first divide, bud color is Red Group 46C.

*Sepals.*—Color: Medium to dark green and turning to a brownish red upon bloom opening. Surface texture: Mostly smooth.

*Peduncle.*—Length: Medium to long. ½ to ¾ inches. Surface: Some prickles. Strength: Stiff. Color: Medium green; sometimes reddish brown.

Bloom:

*Size.*—Small; Average open size is 1.5 inches.

*Borne.*—Singly and sometimes in loose clusters of 2 to 4 flowers.

*Stems.*—Small and strong. Average flowering stem length is about 6 to 12 inches.

*Form.*—High centered; reflexed petals; Exhibition; When fully open stamens show.

*Petalage.*—Double; Number of petals under normal conditions: 17–25. Arranged regularly plus some small petaloids. Petals are thick and velvety on the inside.

*Color.*—The petals' upper side is Red Group 45B. The petals' reverse side is Red Group 46C.

*Variegations.*—None.

*Discoloration.*—The general tonality at the end of the first day: No change. At the end of the third day: No Change.

*Fragrance.*—None.

*Lastingness.*—On plant about 7–10 days on average.

Reproductive parts:

*Anthers.*—Size: Medium; Quantity: Many; Color: Yellow; Arrangement: Regular around styles.

*Filaments.*—Varying length, short to medium long, yellow.

*Pollen.*—Quantity: Heavy; Color: Golden yellow.

*Styles.*—Color: reddish.

*Stigmas.*—Color: whitish.

*Ovaries.*—All enclosed in calyx.

*Hips.*—Dark yellow when ripened.

*Seeds.*—Varying shapes; mostly enclosed but some exogenous.

Growth:

*Habit.*—Dwarf; bushy; upright; vigorous.

Foliage:

*Leaflets.*—Number on normal mid-stem leaves: 5 or 7.

*Size.*—Medium; Leaflets vary in length from 1 to 3 inches.

*Quantity.*—Abundant.

*Color.*—New foliage: Lower and upper surface; Greyed Purple Group 187A.

*Old foliage.*—Upper surface: Green Group 139A. Lower surface: Green Group 139C.

Leaflets:

*Shape.*—Pointed oval.

*Texture.*—Leathery; glossy.
*Edge.*—Serrated.
*Serration.*—Single, small.
*Petiole rachis.*—Smooth with reddish coloration.
*Petiole underside.*—May have several prickles.
*Stipules.*—Medium to short length (½ to ⅝ inch).

Wood:

*New wood.*—Color: Reddish but turns green very quickly.
*Old wood.*—Color: Green; Bark smooth.

Prickles:

*Quantity.*—Ordinary.
*Form.*—Varying sizes from small prickles to medium thorns; Medium thorn size (⅜ to ½ inch); hooked downward.

The miniature rose plant and its flowers as herein described may vary in slight detail due to climatic, soil and cultural conditions under which the variety may be grown; the present description being of the variety as grown at Franklin, Tenn.

The following is claimed:

1. A new and distinct variety of miniature rose plant of hardy, dwarf, bushy upright habit, substantially as illustrated and described, characterized by buds and flowers of exhibition form, essentially medium red in color, with reverse of petals being a deep pink, and further characterized by a plant of well rounded shape, vigorous, with the main stems and shoots being moderately thorny, the said plant being easy to propagate from cuttings, with an abundance of flowers borne singly or several to a stem.

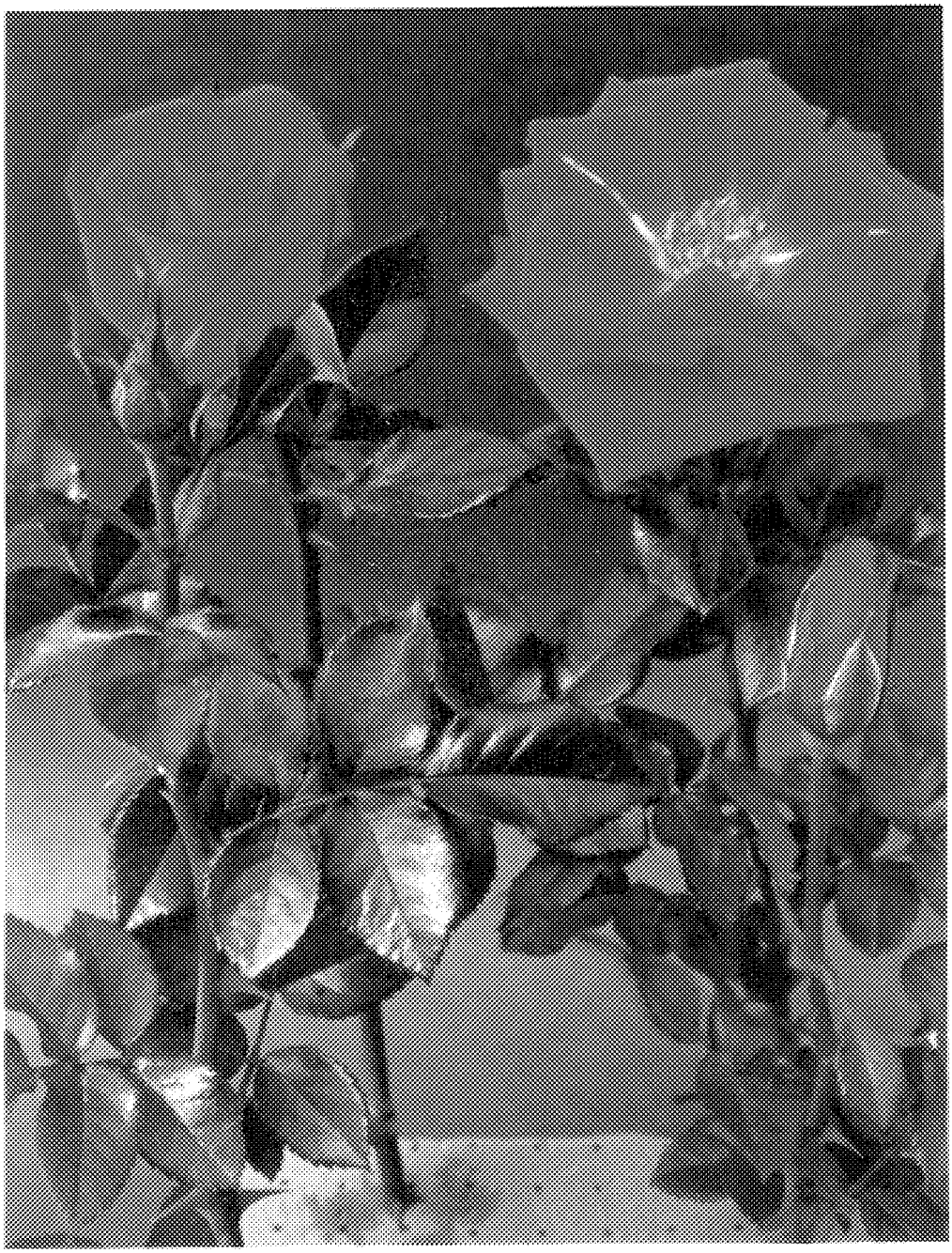

* * * * *